(12) United States Patent
Guillaume Eon et al.

(10) Patent No.: US 12,030,039 B2
(45) Date of Patent: Jul. 9, 2024

(54) CATALYST AND PROCESS OF OXIDATIVE DEHYDROGENATION OF PROPANE

(71) Applicants: PETROLEO BRASILEIRO S.A.—PETROBRAS, Rio de Janeiro (BR); UNIVERISDADE FEDERAL DO ESTADO DO RIO DE JANEIRO—UFRJ, Rio de Janeiro (BR)

(72) Inventors: Jean Guillaume Eon, Rio de Janeiro (BR); Sabrina Sanches Guimaraes, Nova Friburgo (BR); Bernardo Galvao Siqueira, Rio de Janeiro (BR)

(73) Assignees: PETROLEO BRASILEIRO S.A.—PETROBRAS, Rio de Janeiro (BR); UNIVERSIDADE FEDERAL DO ESTADO DO RIO DE JANEIRO, Rio de Janeiro (BR)

( * ) Notice: Subject to any disclaimer, the term of this patent is extended or adjusted under 35 U.S.C. 154(b) by 392 days.

(21) Appl. No.: 17/413,817

(22) PCT Filed: Dec. 16, 2019

(86) PCT No.: PCT/BR2019/050540
§ 371 (c)(1),
(2) Date: Jun. 14, 2021

(87) PCT Pub. No.: WO2020/124182
PCT Pub. Date: Jun. 25, 2020

(65) Prior Publication Data
US 2022/0016606 A1    Jan. 20, 2022

(30) Foreign Application Priority Data
Dec. 17, 2018 (BR) .......................... 102018076221-4

(51) Int. Cl.
*B01J 27/18* (2006.01)
*B01J 37/03* (2006.01)
*B01J 37/04* (2006.01)
*B01J 37/08* (2006.01)
*C07C 5/48* (2006.01)

(52) U.S. Cl.
CPC ......... *B01J 27/1806* (2013.01); *B01J 37/031* (2013.01); *B01J 37/04* (2013.01); *B01J 37/08* (2013.01); *C07C 5/48* (2013.01)

(58) Field of Classification Search
CPC ....... Y02P 20/52; B01J 35/002; B01J 37/031; B01J 37/04; B01J 37/08; B01J 37/343; B01J 23/002; B01J 23/16; B01J 23/30; B01J 23/20; B01J 23/22; B01J 23/24; B01J 27/1806; B01J 27/186; B01J 27/188; B01J 27/195; B01J 27/198; B01J 27/199; C07C 2527/199; C07C 2527/198; C07C 2527/195; C07C 2527/188; C07C 2527/186; C07C 5/48
USPC ........ 502/209, 210, 211, 305, 306, 311, 312
See application file for complete search history.

(56) References Cited

U.S. PATENT DOCUMENTS

| 2014/0114109 A1 | 4/2014 | Sanchez Valente et al. |
| 2017/0226030 A1 | 8/2017 | Li et al. |

FOREIGN PATENT DOCUMENTS

| BR | 102013019137 A2 | 8/2015 |
| WO | 2014134703 A1 | 9/2014 |
| WO | 2016049144 A1 | 3/2016 |

OTHER PUBLICATIONS

Tegg et al., "The sodium tungsten bronzes as plasmonic materials: fabrication, calculation and characterization", Mater. Res. Express 4 (2017) 065703.*
Pinheiro et al., "Isomer distribution in a-Keggin structures," C. R. Chimie 19: 1352-1362 (2016).
Udalova et al., "The influence of additives and their concentration on the selectivity of catalysts based on heteropoly compounds in the reaction of propane oxidation," Catalysts in Industry 2(1): 38-41 (2010).
International Search Report in International Application PCT/BR2019/050540, dated 2019-02-19.

* cited by examiner

*Primary Examiner* — Elizabeth D Wood
(74) *Attorney, Agent, or Firm* — RAPHAEL BELLUM PLLC; Andrew C. Stoner

(57) ABSTRACT

The present invention refers to catalysts that are selective for the reaction of ODH of propane to propene. Said catalysts are potassium salts of the dodecatungstophosphate ion partially substituted with vanadium and niobium, or mixed oxides of W, V, and Nb, with a tungsten bronze structure, obtained by thermal decomposition of polyoxometalate salts with a Keggin structure.

3 Claims, 9 Drawing Sheets

CATALYST AND PROCESS OF OXIDATIVE DEHYDROGENATION OF PROPANE

FIELD OF THE INVENTION

The present invention refers to the production of propene from propane using potassium salt catalysts. More precisely, the present invention refers to the preparation of potassium salts from the dodecatungstophosphate ion partially substituted with vanadium and niobium, or mixed oxides derived, with structure of tungsten hexagonal bronzes and its application to the production of propene through oxidative dehydrogenation (ODH) of propane.

BACKGROUND OF THE INVENTION

Oxidation catalysis is a technology of main importance in the chemical industry by the enormous possibilities of application in obtaining large, aggregated value products. In addition, there is particular interest in the functionalization of aromatics obtained directly from petroleum or natural gas and from alkanes, the demand of which has increased primarily by the lower cost and toxicity relative to olefins.

Among the oxidation reactions, the oxidative dehydrogenation of alkanes of short carbon chain leading to formation of olefins has particular interest. These olefins find important applications in the industrial synthesis of polyethylene or polypropylene for the manufacture of plastics and fibers, or as a chemical intermediate in the synthesis of acetone, isopropanol, halides, acrylonitrile among others.

Unlike the oxidation reaction of propane to acrylic acid, it has not yet found patent filing claiming an economically viable catalytic formula for the production of propene via the ODH reaction of propane. Publications in the open literature report mainly studies of the reaction mechanism, seeking to evaluate the major factors responsible for defining the selectivity of the catalyst relative to propene. Most published works analyse the role of V or Mo in bulk or supported mixed oxides, since these elements provide increased activity and selectivity to the catalyst than other transition metals. Thus, it is sought to use ternary or quaternary mixed compositions of these elements to isolate bridging oxygens shared by two or three vanadium atoms. The introduction of catalytically active metal elements into a well-defined and controlled composition polyanion allows obtaining homogeneous composition oxides after their thermal decomposition.

The prior art describes numerous heterogeneous catalysts employed in the ODH reaction of propane, but none has a satisfactory combination of activity and selectivity.

In this regard, the document Heteropoly 12-Metallophosphates Containing Tungsten and Vanadium. Preparation, Voltammetry, and Properties of Mono-, Di-, Tetra- and Hexavanade Complexes (M. T. Pope, D Smith. Inorganic Chemistry, 12, No. 2, 1973), describes the obtention of polyoxometalates salts having Keggin structure mixed with composition of $PV_4W_8O_{40}$. However, there is no systematic study allowing deducing the structure of the mixed oxide obtained by thermal decomposition of polyoxometalates salts.

Since the document "Multi-Element Crystalline and Pseudocrystalline Oxydes as Efficient Catalysts For the Direct Transformation of Glycerol into Acrylic Acid" (A. Chieregato, M. D. Soriano, E. Garcia-González, G. Puglia, F. Basile, P. Concepción, C Bandinelli, J. M. L. Nieto, F. Cavani, ChemSusChem, 8, p. 398-406, 2015) describes obtaining catalysts of mixed oxides based on tungsten, molybdenum and vanadium showing the hexagonal bronze structure. In this document, the authors characterize and evaluate the catalytic properties of mixed oxides in the W—Mo—V—O system in the oxidehydration reaction of glycerol to acrylic acid. The reported materials show a Mo/W ratio greater than 20% and variable structure as a function of V and Mo contents. It is noted that the selective materials in the reaction do not show the hexagonal bronze structure, but rather a structure called pseudo-crystalline structure, correlated with the phase named Mi (type $M_5O_{14}$) in literature. As a number of mixed oxides formed by the start-of-period transition metals, the crystalline structure of the corresponding phase is correlated to the structure $ReO_3$, where metals having octahedral coordination share only the vertices of the coordination polyhedron. In this document, the catalysts effectively have a hexagonal bronze structure of tungsten, however, the vanadium is with +4 oxidation number, since vanadyl sulfate $VOSO_4$ is employed as a vanadium source. The reduction of vanadium is essential for the formation of the bronze phase in these conditions.

In addition, the document "Thermal decomposition behavior of metal-oxygen clusters with Keggin Structure" (Kong, A G et al. Chemical Journal of Chinese University-Chinese 1 26 (11): 2002-2006 Nov. 10, 2005), evaluated the behavior of polyoxometalates with Keggin structure after treatment at various temperatures. The most significant case in this document refers to thermal decomposition of potassium salt $K_3PW_{12}O_{40}$, where it is possible to verify, in FIG. 1(c), that the salt remains stable to the temperature of 800° C., but is decomposed at 900° C., only having indication of formation of $WO_3$ (which has several allotropic varieties) and perhaps of $K_2WO_4$. In FIG. 1 it is possible to distinguish a peak around 14° and three peaks just below 25° (at 2 theta), the first peak being only in the hexagonal phase (as the base ICSD-Inorganic Crystal Structure Database), but the second group of peaks indicate a triclinical or monoclinic phase, therefore incompatible with the desired hexagonal phase. Furthermore, the relative intensities of the four peaks are not in accordance with the intensities of the hexagonal phase, or a mixture of phases.

On the other hand, U.S. Pat. No. 8,105,972 (B2) describes a process for the formation of catalysts useful for the conversion of paraffins to olefins within a wide range of composition (Mo—V—X—Y—O). More specifically, it refers to the preparation of catalysts useful for oxidative dehydrogenation (ODH) of hydrocarbons to form olefins, more precisely ethene. It is noted, however, that all of the substantial examples refer to oxides properties in the system Mo—V—Nb—Te with Mo/V ratio near 3, in the ODH reaction of ethane to ethene. In these materials, the dominant element is Mo, and, unlike the present invention, the catalysts do not show potassium in the composition thereof.

Confirming the validity of the strategy, it was observed that the mixed oxides of vanadium and tungsten, deposited in gamma-alumina adsorbing substituted Lindqvist ions $V_xW_{6-x}O_{19}$ (x=1,2), led to improved catalyst performance in the ODH Reaction of propane (Kaezer Franga M. C., Aguiar da Silva San Gil R., Eon J.-G., Catal. Today 78 (2003) 105). The hexametalate, still called the polyanion of Lindqvist, however, is limited to binary compositions with the cited two stoichiometric ratios and does not show the versatility of chemical composition, for example, of the polyanion of Keggin.

By addressing the above-mentioned drawbacks of Lindqvist ions, catalysts have been developed, objects of the present invention, For application in the reaction of ODH de propane to propene.

Thus, it is possible to note that there are no reports in the state of the art that anticipate the preparation of catalysts obtained by thermal decomposition of polyoxometalates salts of the series of Keggin based on tungsten, niobium and vanadium, as well as its application in a propene production process by oxidative dehydrogenation of propane.

SUMMARY OF THE INVENTION

The present invention refers to catalysts of mixed oxides of tungsten (W), niobium (Nb), vanadium (V), in the form of potassium salts of the dodecatungstophosphate ion partially replaced with vanadium and niobium, or oxides derived from the structure of tungsten bronzes, useful in the oxidative dehydrogenation reaction (ODH) of propane to propene.

Such catalysts are prepared by direct synthesis in aqueous solution of polyoxometalates salts of W, Nb e V, with Keggin structure (FIG. 1a), which upon undergoing thermal decomposition lead to the formation of mixed oxides of W, Nb and V, having structure of tungsten bronzes (FIG. 1b).

The objects and other advantages of present invention will become more apparent from the following description and the accompanying drawings.

BRIEF DESCRIPTION OF THE FIGURES

The detailed description set forth below refers to the accompanying figures in which.

DETAILED DESCRIPTION OF THE INVENTION

The present invention refers to the synthesis and characterization of potassium salts of the dodecylmercaptan ion partially substituted with vanadium and niobium and mixed oxides W, V and Nb derived, with structure of tungsten bronzes for use in the ODH reaction of propane to propene.

A first object of present invention is the description of such catalysts prepared from the thermal decomposition of polyoxometalates (POM) salts of Keggin type structure based on W, V and Nb.

Figure 1A:
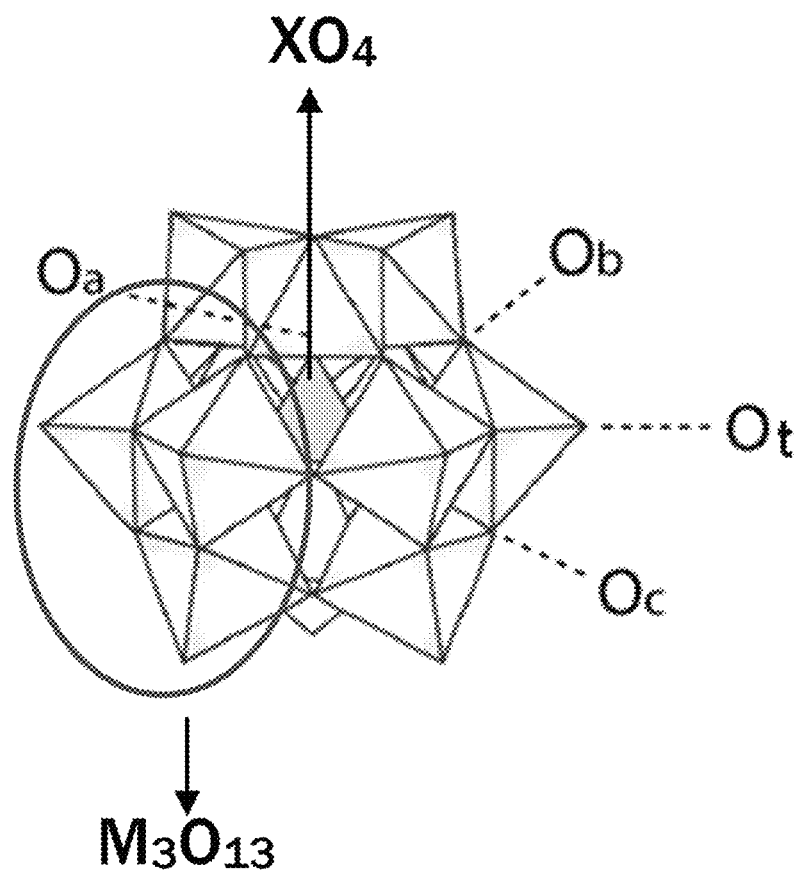
FIGS. 1a-1b depicts the structure of isomer of Keggin ion, of general formula $XM_{12}O_{40}$, demonstrating the connections among the four octahedra groups $M_3O_{13}$ bonded by the vertices. These $M_3O_{13}$ groups bind to the $XO_4$ tetrahedron completing the structure thereof. In this ion, X can correspond to P, Si, Ge and M represent transition metals such as W, Mo, which may be partially replaced with Nb, V or even Cu, Ni, etc (FIG. 1a), the Keggin ion can undergo thermal decomposition which leads to the formation of mixed oxides of W, Nb and V, having structure of tungsten bronzes (FIG. 1b).
Figure 1B:
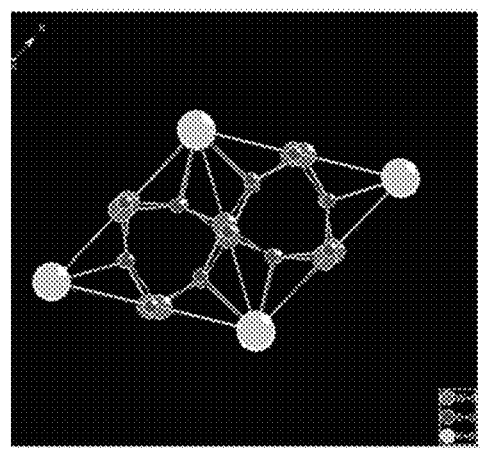
Figure 2:
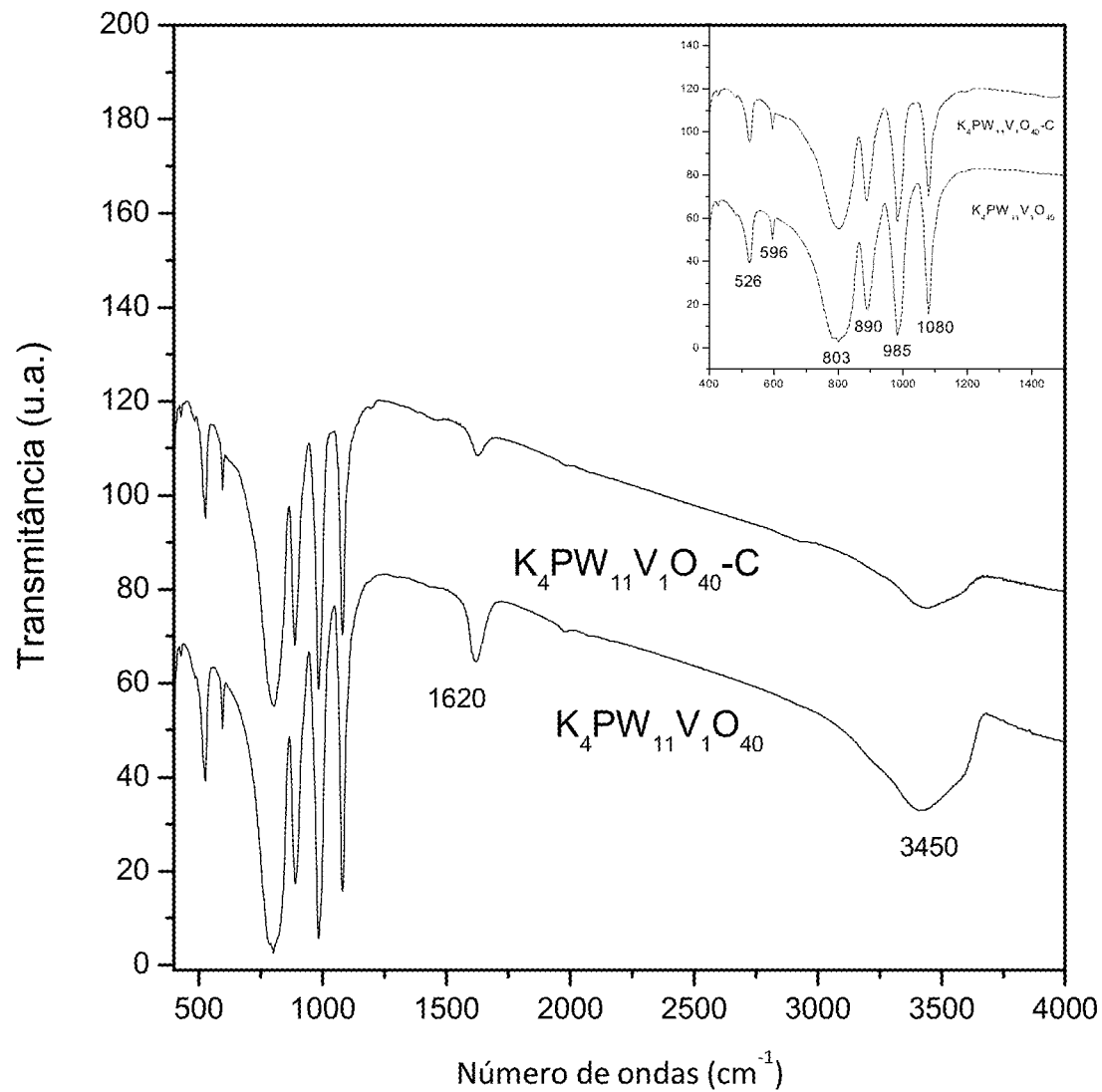
FIG. 2 depicts Infrared absorption spectra of the polyoxometalates.

The Keggin type structure is illustrated in FIG. 1, where it can be seen that the polyoxometalate of general formula $[XM_{12}O_{40}]^{-n}$, where X=K, and M=W, V and Nb, and note the connections between the four octahedra groups $M_3O_{13}$ bonded by the vertices. In this type of structure, the $M_3O_{13}$ groups bind to the $XO_4$ tetrahedron and the oxygen atoms are classified into four types, $O_a$, $O_b$, $O_c$, and $O_d$ or $O_t$, according to the type of bond. The oxygen atom identified by $O_a$ refers to oxygen that is bonded to the central atom and shared by a Group $M_3O_{13}$, the one represented by $O_b$ is bonded to two metal atoms of different $M_3O_{13}$ groups, the one identified by $O_c$ refers to the oxygens bonded to two metal atoms of the same Group $M_3O_{13}$ and $O_d$ or $O_t$ are the oxygen atoms bonded to a metal atom, that is, oxygens in terminal position.

However, to obtain a propene-selective catalyst in ODH reactions, it is necessary that there are available oxygens on the catalyst surface, which can be achieved by the presence of more reducible oxides, and therefore more active, such as vanadium oxide is, relative to, for example, niobium and tungsten oxides.

Thus, when using ternary mixed compositions of W, V, and Nb, as proposed in the present invention, isolation of the bridging oxygen atoms shared by two or three vanadium atoms is promoted, which ultimately increases the selectivity of the catalyst in this type of reaction.

Further, in addition to increased selectivity, another important characteristic for a catalyst is the maintenance of the activity thereof when subjected to high reaction temperatures, which in this case range from 350 to 550° C.

Such catalysts useful in the reaction of oxidative dehydrogenation reaction (ODH)) of propane are described below, according to their preparation, which comprises the thermal decomposition of polyoxometalates salts of Keggin type structure based on tungsten, vanadium and niobium represented by the general formula $[PW—V_xNb_yO_{40}]^{n-}Z^{m+}$, where 1≤x≤6; y≤3 and 4≤m≤n≤11, Z being an alkali metal among: Na, K or Cs or alkaline earth metal chosen among: Mg, Ca, Ba in order to obtain mixed oxides of W, V, and Nb.

The preferred route for preparing the mixed oxides of W, V, and Nb for use in propane oxidative dehydrogenation reactions comprises the following steps:

a) dissolving alkali or alkaline earth metal salts of oxometallates of W, V, and Nb, in water at a temperature ranging from 40 to 80° C. the molar ratios W:V and V:Nb being from 2 to 8, so that an aqueous solution of polyoxometalates is obtained wherein the mass ratio of the oxometallates to water is between 30 and 40% m/m;

b) adding to the aqueous solution obtained in step (a) an inorganic acid to a pH between 6.5 and 7.5, and heating the solution to temperatures from 150 to 180° C. for a period of time ranging from 3 to 4 hours;

c) adding, under constant agitation, to the aqueous solution obtained in (b) a saturated solution of an alkali or alkaline earth metal salt, in an amount of 60 to 80% v/v of polyoxometalates solution relative to the saturated solution until precipitation of mixed salts of polyoxometalates of tungsten, vanadium and niobium occurs;

d) filtering and drying the polyoxometalates salts obtained in step (c) at a temperature ranging from 25 to 50° C.

e) promoting calcination of the materials obtained in (d) under air flow at temperatures from 350 to 550° C. for a period of time from 3 to 5 hours to obtain mixed Oxides of W, V, e Nb, with structure of tungsten bronzes.

Preferably, the alkali or alkaline earth metal salts employed in step (a) of the process are those selected from: $NaWO_4$, $NaVO_3$, and $(NH_4)_3[NbO(C_2O_4)_3]\cdot 2H_2O$.

For pH correction, described in step (b) of the process, and responsible for the formation of the heteropolyanion of keggin, inorganic acids are used, selected from: HCl, $HNO_3$ and $H_3PO_4$.

It is preferably used in step (c) salts of metals: KCl or KNO$_3$, as they do not alter the pH of the solution and lead to precipitation of the polyoxometalates.

Figure 3:
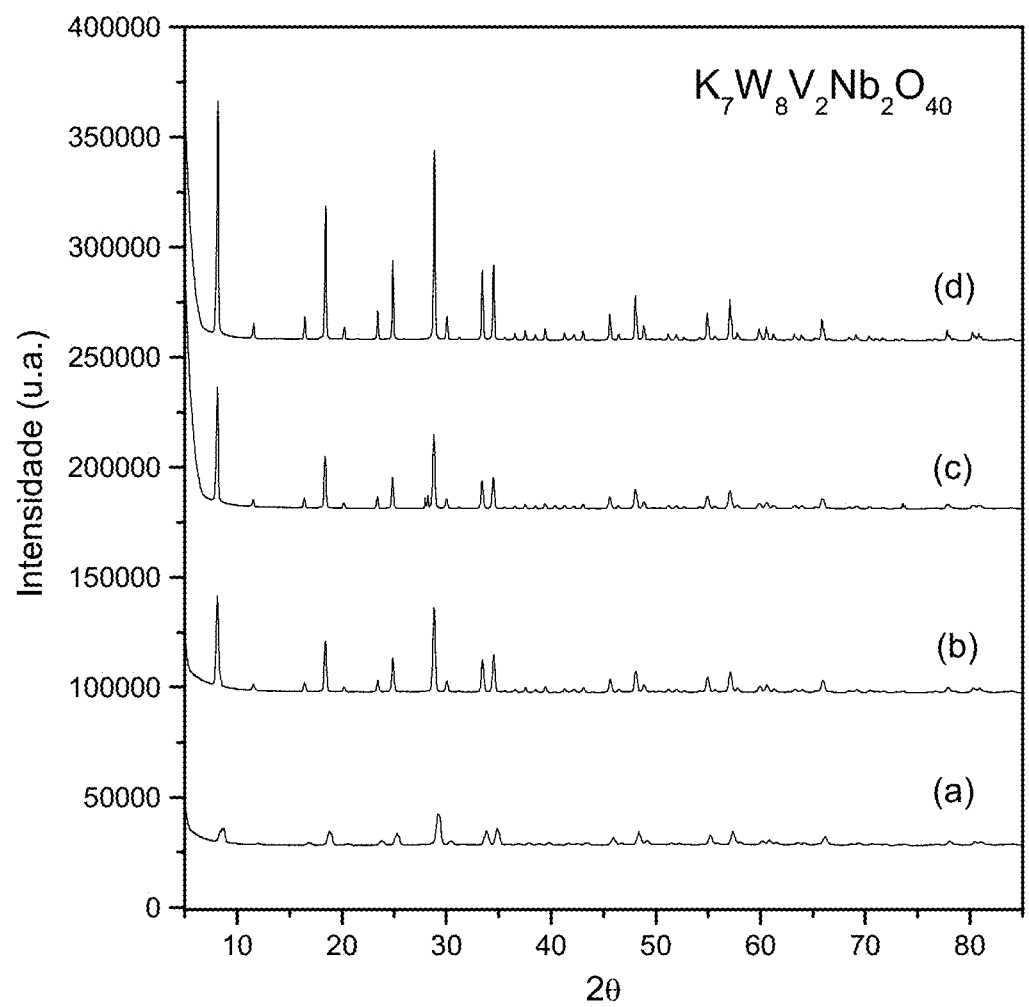
FIGS. 3 through 7 depict X-ray diffractograms and simulations for the various catalysts of present invention.
Figure 3:
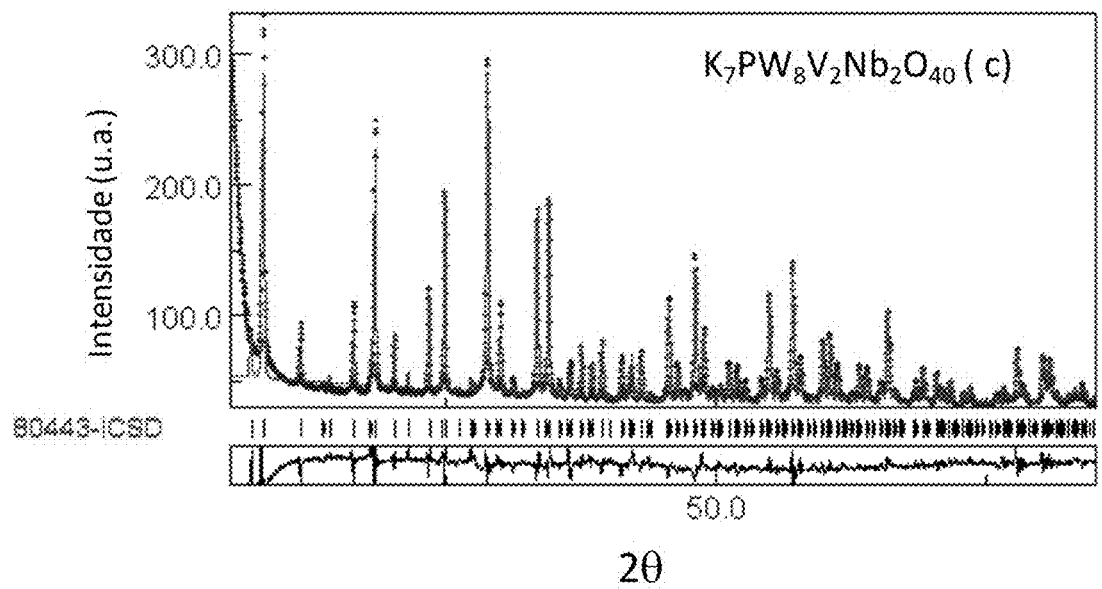
Figure 4:
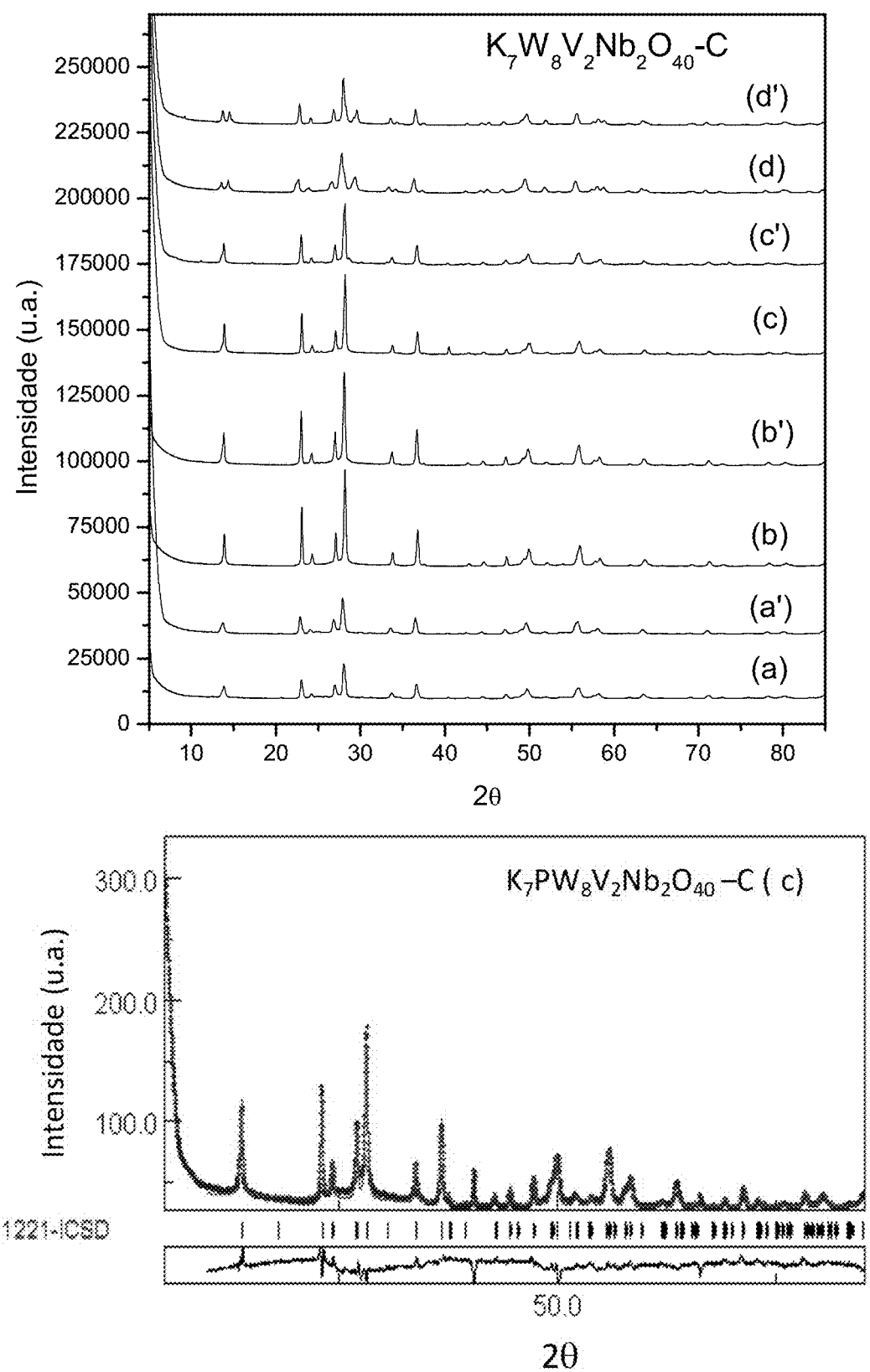
Figure 5:
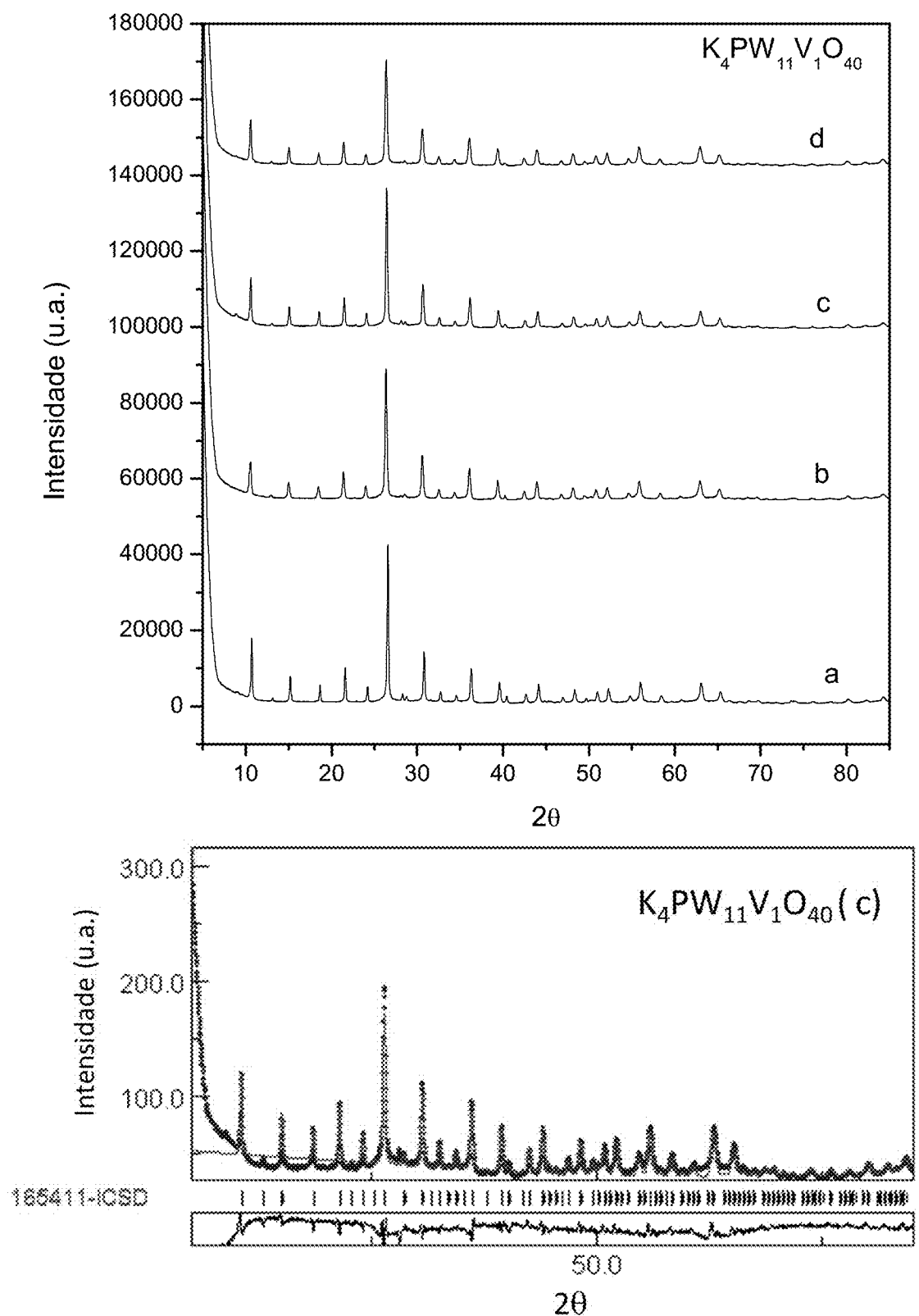

The tungsten bronzes structure of such mixed oxides are believed to be responsible for increased selectivity in the conversion of propane to propene in ODH reactions due to the isolation of active sites, which leads to an increase of available oxygens on the catalyst surface, in a sufficient number to activate and oxidize the hydrocarbon molecule without it being overoxidized, which is illustrated by FIGS. 3 and 4 and Table 3.

FIG. 3, for example, shows X-ray diffractograms for the potassium salts of Keggin polyanion replaced with V, and Nb of chemical formula K$_7$PW$_8$V$_2$Nb$_2$O$_{40}$, corresponding to four different syntheses, identified by letters a, b, c, or d, with change in the niobium source in synthesis d. Although most samples show the characteristic peaks of the phase corresponding to the X-ray diffraction pattern ICSD 80443 (inorganic crystal structures database—the standard corresponds to the isomorphous phase K$_6$[PMo$_3$W$_9$O$_{40}$]·13H$_2$O), the different reported intensities indicate changes in catalyst crystallinity, in turn leading to variations in their catalytic performance in the ODH reaction of propane, which demonstrates that the catalyst structure influences the achieved results.

FIG. 4, in turn, shows the X-ray diffractograms (DRX) for the same calcined samples K$_7$PW$_8$V$_2$Nb$_2$O$_{40}$—C, where the term —C is relative to calcination, and identified by the corresponding synthesis code (a, b, c, d) and for the same samples used in the catalytic test (a', b', c', d'). All the samples showed the characteristic peaks of the hexagonal bronze phase of tungsten according to ICSD 61222 standard. No significant change in the phase of the catalysts was observed in the DRX results between the respective calcined samples and those used in the catalytic test. From Table 3 it is possible to note that the structural stability of the catalyst during the ODH reaction of propane at the investigated conditions, especially when comparing the calcined sample (identified in Table 3 as (C)) and that used in the catalytic test (identified in Table 3 as (TC)).

It is a further object of the present invention to provide an oxidative dehydrogenation process of propane, wherein the selectivity is greater than 60% for conversions up to 50%, especially due to the effect caused by the tungsten bronze structure of the catalysts employed.

The process applies preferably to feedstocks comprising a mixture of propane and air in a volume ratio ranging from 1 to 3%.

For the promotion of the reaction, the charge is fed into a fixed bed reactor that operates under the following conditions: GHSV from $10^3$ to $10^4$ h$^{-1}$, atmospheric pressure, and temperatures ranging from 350 to 520° C.

Figure 6:
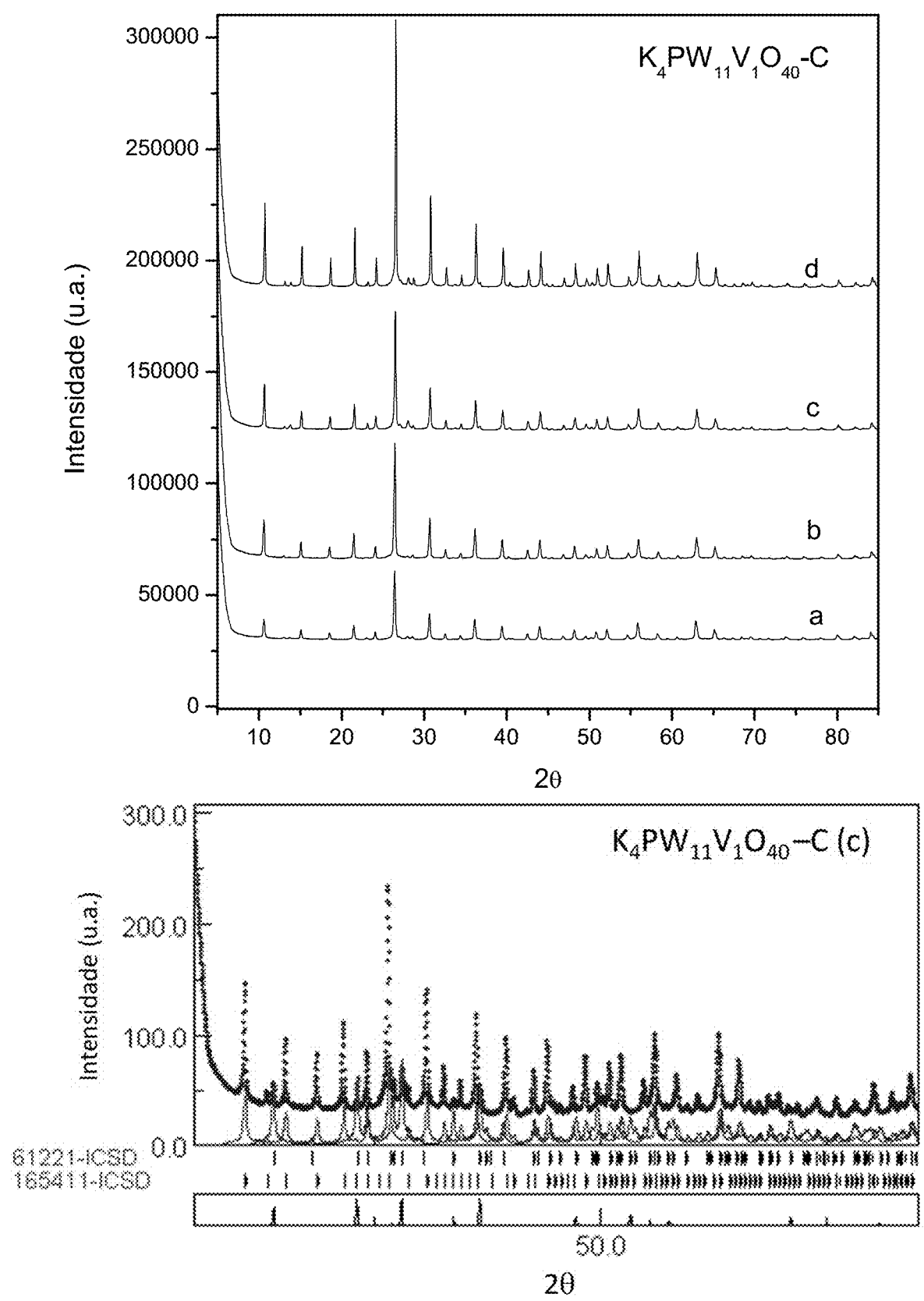
Figure 7:
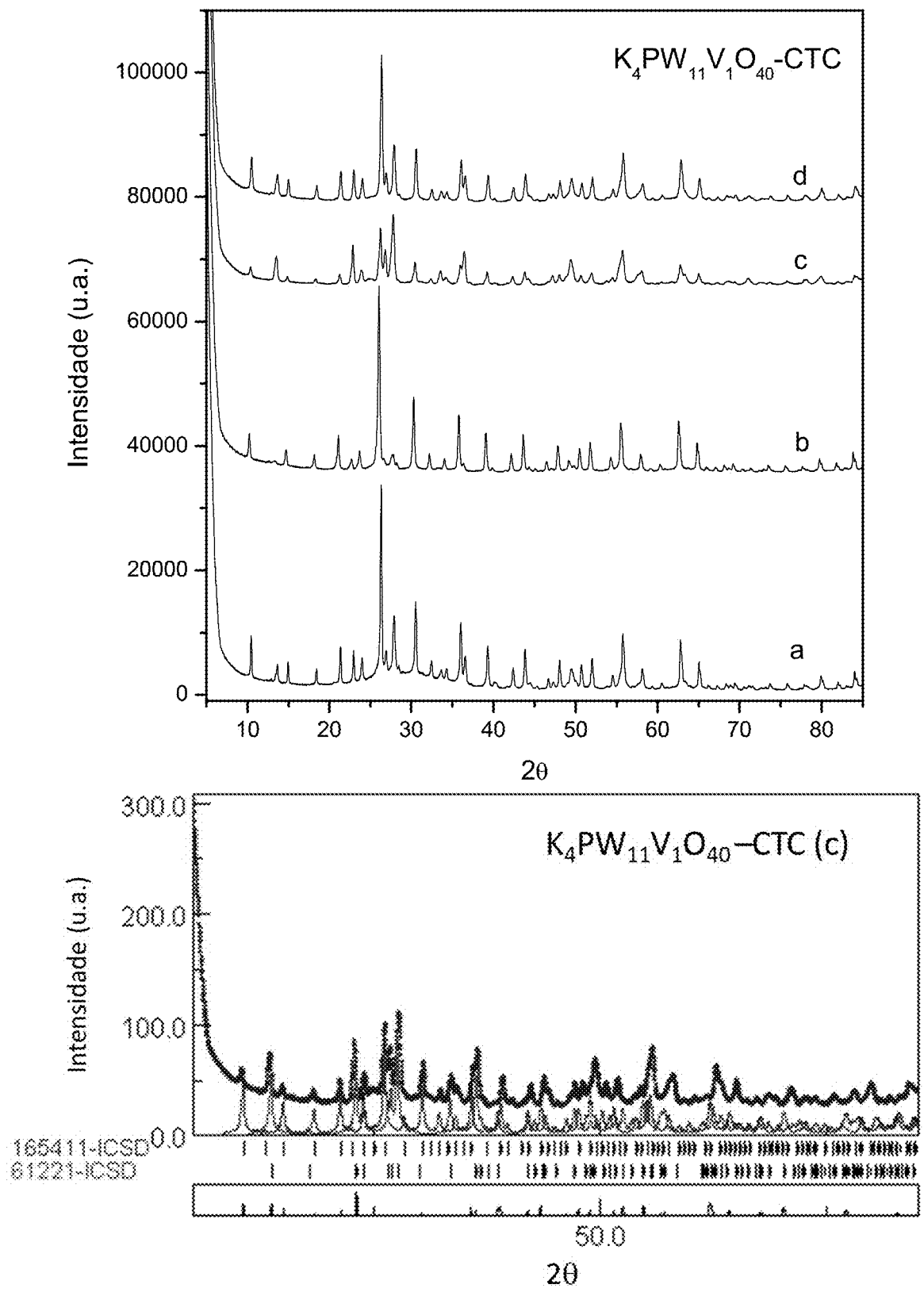

FIGS. 6 and 7 show X-ray diffractograms for the calcined samples K$_4$PW$_{11}$V$_1$O$_{40}$—C and used in the catalytic test (CTC). It is possible to observe the appearance of the peaks of the hexagonal bronze of tungsten (HTB) beside the peaks of the potassium salt of the Keggin ion, with the predominance of the Keggin ion salt. The results for the samples used, after the catalytic test, show a significant increase in the bronze phase (HTB) present in those samples. This shows that the catalyst does not have stable structural during the ODH reaction, however, they show stable conversion and selectivity results during the analysis time.

The following description will start from preferred embodiments of the invention. As will be evident to any technician in the matter, the invention is not limited to those particular achievements.

EXAMPLES

Synthesis of Catalysts:

The step (a) of tungsten and vanadium-based polyoxometalate was performed from 1.3943 g of sodium metavanadate (NaVO$_3$) that was dissolved in 8 mL of water and 6.3149 g of sodium tungstate dihydrate (Na$_2$WO$_4$·H$_2$O) that were dissolved in 10 mL of water, previously heated to 60° C. Then, phosphoric acid (H$_3$PO$_4$—85%) was slowly added until the pH of 7.5 was reached. The solution was transferred to the teflon reactor and kept in the microwave equipment at a temperature of 175° C. for 1 hour.

The step (a) of tungsten, vanadium and niobium-based polyoxometalate, followed the same procedure, but initially 0.6971 g of NaVO$_3$ were used, which were dissolved in 4 mL of water and 1.8335 g of niobium ammoniacal oxalate (NH$_4$)$_3$[NbO(C$_2$O$_4$)$_3$)]·2H$_2$O which were dissolved in 4 mL of water, previously heated to 60° C.

Step (b) consists of the excess addition, after cooling, of potassium chloride (KCl), that is, 1 g of solid and 9 g of a saturated solution, in order to start precipitation. The precipitate is under constant agitation for 30 minutes and then filtered and dried in an oven at 80° C.

Step (c) consists of thermal degradation (calcination) of polyoxometalate salts at 500° C., with heating rate of 5° C./min in synthetic air atmosphere with flow of 30 mL/min for 3 hours.

Table 1 shows the results of the chemical analyses performed by x-ray fluorescence technique for the various catalysts of series 1, K$_7$PW$_8$V$_2$Nb$_2$O$_{40}$. The results show a variation in the experimental molar content of niobium inserted in the samples, and sample d shows the composition closest to the ideal value. Samples a, b, and c were prepared using the same procedure and reagents, but in the niobium source sample it was replaced, and an ammoniacal niobium salt instead of niobium oxide was used. That change was probably responsible for the greater insertion of Nb in the structure.

TABLE 1

Chemical Composition of Catalyst Series 1

| Samples | Experimental Molar Ratio | | Experimental Stoichiometry | | | |
|---|---|---|---|---|---|---|
| | W/V | V/Nb | K | V | W | Nb |
| K$_7$PW$_8$V$_2$Nb$_2$O$_{40}$(a) | 4.3 | 3.0 | 5.8 | 2.1 | 9.1 | 0.7 |
| K$_7$PW$_8$V$_2$Nb$_2$O$_{40}$(b) | 3.1 | 3.0 | 6.1 | 2.7 | 8.4 | 0.9 |
| K$_7$PW$_8$V$_2$Nb$_2$O$_{40}$(c) | 3.2 | 2.9 | 7.5 | 2.6 | 8.4 | 0.9 |
| K$_7$PW$_8$V$_2$Nb$_2$O$_{40}$(d) | 3.7 | 1.3 | 5.6 | 2.2 | 8.1 | 1.7 |

Table 2 shows the results of the chemical analyses performed by x-ray fluorescence for the samples series 2, with W:V ratios equal to 11:1. The experimental results show vanadium content lower than the theoretical ratio. However, these results show that the reproducibility of the synthesis can be achieved.

TABLE 2

Chemical Composition of Catalyst Series 2

| Samples | Experimental Stoichiometry | | |
|---|---|---|---|
| | K | V | W |
| $K_4PW_{11}V_1O_{40}$ (a) | 4.6 | 0.2 | 11.8 |
| $K_4PW_{11}V_1O_{40}$ (b) | 3.3 | 0.2 | 11.8 |
| $K_4PW_{11}V_1O_{40}$ (c) | 4.0 | 0.5 | 11.5 |
| $K_4PW_{11}V_1O_{40}$ (d) | 3.9 | 0.3 | 11.6 |

Test of Catalyst in the Reaction of Interest:

To illustrate the higher efficiency of the catalysts tested in the present invention, tests were performed in the ODH reaction of propane using a conventional flow system. 500 mg of catalyst was deposited in a fixed U-shaped bed reactor, made of pyrex or quartz, operating under atmospheric pressure and fed by a mixture of 1% (v/v) of propane/synthetic air. The flow of the mixture was fixed at 30 mil/min by a Brooks mass flow controller. The reagent ($C_3H_8$) and the reaction products ($C_3H_6$, $CO_2$ and CO) were analyzed online in an Agilent GC-7820A chromatograph. In this analysis, the gas sample passes through a metanator after separation of the gaseous components by a Porapak Q capillary column and before the FID detector. The carbon balance reached 100% according to the experimental errors of the system.

The tests were performed with increasing temperature in a range between 300 and 550° C. About 15 min after reaching the reaction temperature, 3 injections were performed at intervals of 15 min, amounting to 45 min of reaction: the result shown corresponds to the mean of these 3 injections for each temperature. The catalysts under study showed a relevant stability, in a satisfactory range of conversion and selectivity for a more in-depth study of industrial interest.

In the examples reported in present invention, the ODH reaction of propane produced only propane and carbon oxides. The propane selectivity was quantified by gas chromatography, and for most samples, selectivity was above 70%.

Figure 8:
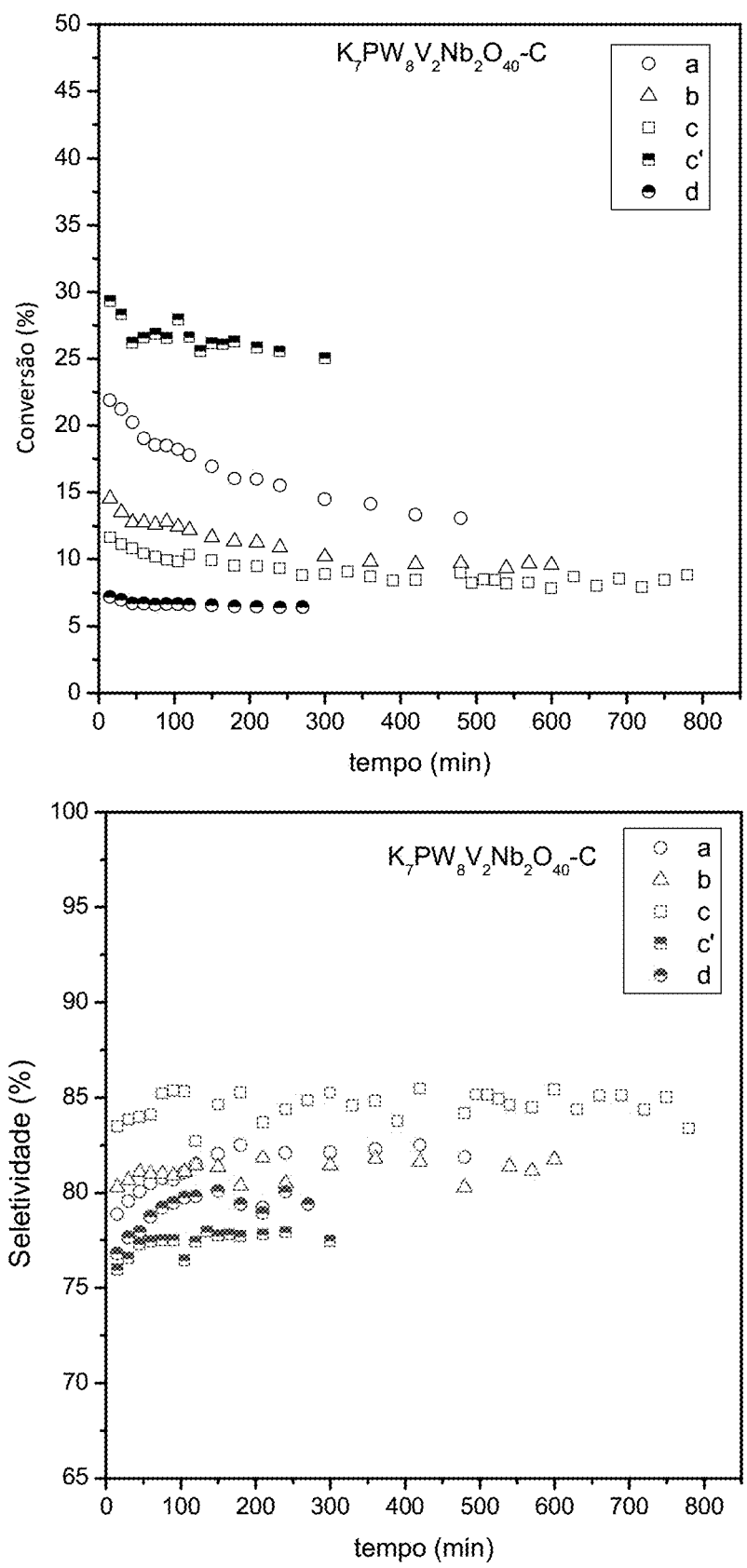
FIGS. 8 and 9 depict the stability curves for propane conversion and propene selectivity as a function of analysis time.
Figure 9:
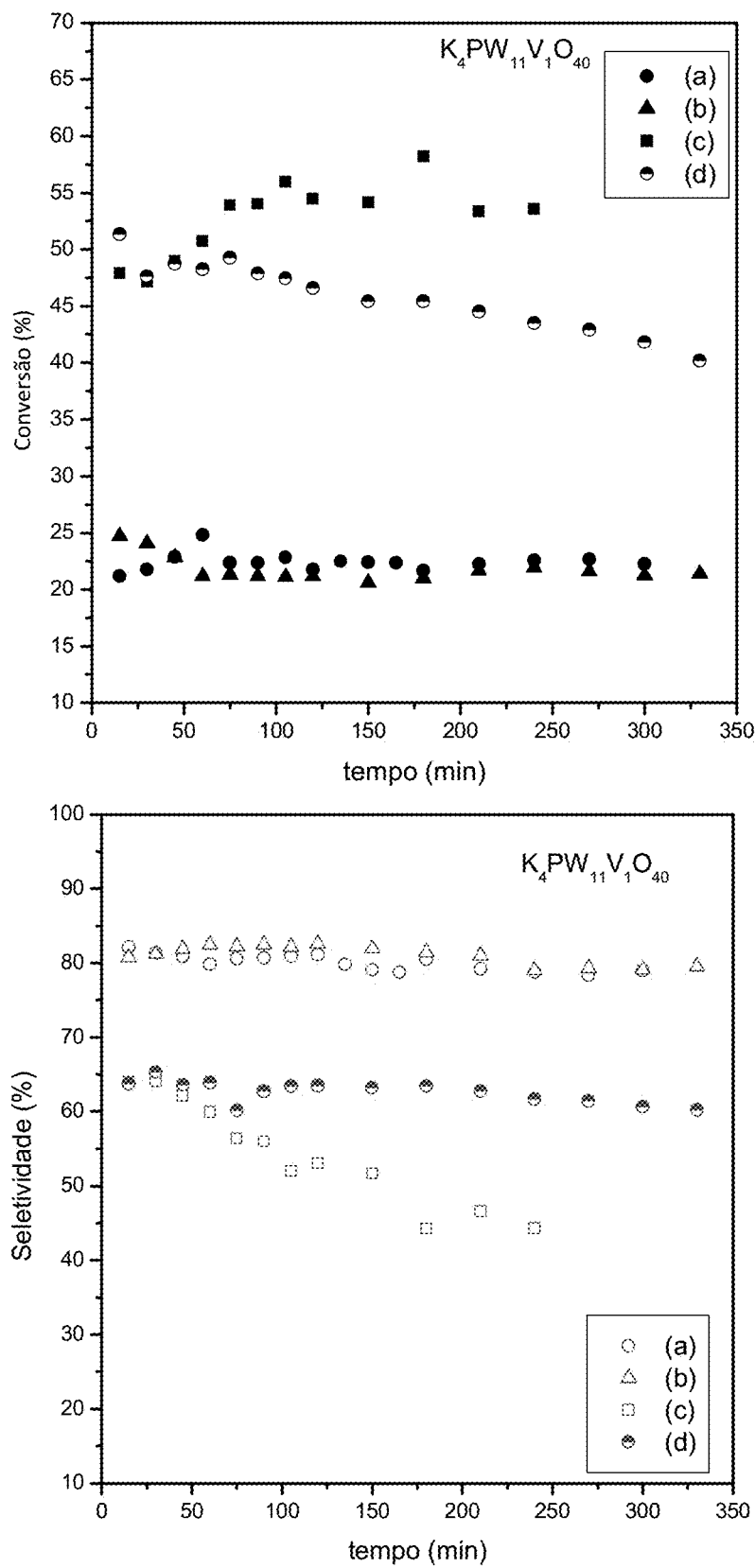

Table 3 shows the results of catalytic tests for propane ODH reaction as a function of temperature for the various samples described. As can be observed, the conversion increases with increasing temperature for all samples reaching a maximum conversion at 490° C. of 28% and 49%, respectively for samples $K_7PW_8V_2Nb_2O_{40}$ (c') and $K_7PW_8V_2Nb_2O_{40}$ (d). Although the previous samples had high conversions, the best values for propane selectivity, around 80%, were obtained for samples having lower conversions, around 11% $K_7PW_8V_2Nb_2O_{40}$ (c) and 22% $K_7PW_8V_2Nb_2O_{40}$ (a and b)), but which remained stable throughout the 300 minutes of analysis, as shown in FIGS. 8 and 9. For the conditions of analysis, the yields around 20% are satisfactory showing the great potential of these catalysts for use on an industrial scale. The BET surface area for niobium-based samples did not show significant values and for samples with W:V ratios equal to 11:1 only one measurement was performed, since the chemical compositions are similar. The calcined sample showed a specific area equal to 5.9 $m^2/g$; in the same sample; after the catalytic test there was a specific area reduction to 2.2 $m^2/g$.

TABLE 3

Results of catalytic test

| Samples | Flow Rate (mL/min) | Mass of cat. (g) | BET surface area ($m^2/g$) | T (° C.) | Conversion (%) | Propene selectivity (%) | $CO_2$ selectivity | Propene Yield (%) |
|---|---|---|---|---|---|---|---|---|
| $K_7PW_8V_2Nb_2O_{40}C$(a) | 30 | 0.50 | <0.2 | 450 | 3.3 | 79.7 | 21.3 | 2.6 |
| | | | | 500 | 21.1 | 79.5 | 20.5 | 16.8 |
| $K_7PW_8V_2Nb_2O_{40}C$(b) | 30 | 0.50 | <0.2 | 450 | 1.7 | 82.8 | 17.2 | 1.4 |
| | | | | 480 | 5.6 | 85.7 | 17.3 | 4.6 |
| | | | | 500 | 13.6 | 80.7 | 19.3 | 11.0 |
| | | | | 520 | 17.9 | 76.3 | 23.7 | 13.6 |
| $K_7PW_8V_2Nb_2O_{40}C$(c) | 30 | 0.50 | <0.2 | 450 | 1.9 | 84.8 | 15.2 | 1.6 |
| | | | | 490 | 11.2 | 83.7 | 16.3 | 9.4 |
| $K_7PW_8V_2Nb_2O_{40}C$(c) repetition | 30 | 0.50 | <0.2 | 450 | 4.6 | 81.7 | 18.3 | 3.8 |
| | | | | 490 | 27.9 | 76.6 | 23.4 | 21.4 |
| $K_7PW_8V_2Nb_2O_{40}C$(d) | 30 | 0.36 | <0.2 | 450 | 3.1 | 69.7 | 30.3 | 2.2 |
| | | | | 490 | 6.9 | 77.4 | 22.6 | 5.4 |
| $K_7PW_8V_2Nb_2O_{40}$(a)C | 30 | 0.50 | 5.9 (C) | 450 | 5.3 | 84.2 | 15.8 | 4.5 |
| | | | 2.2 (TC) | 490 | 21.9 | 81.3 | 18.6 | 17.9 |
| $K_7PW_8V_2Nb_2O_{40}$(b)C | 30 | 0.50 | ND | 450 | 7.8 | 82.4 | 17.6 | 6.4 |
| | | | | 490 | 23.9 | 81.3 | 18.7 | 19.4 |
| $K_7PW_8V_2Nb_2O_{40}$(c)C | 30 | 0.50 | ND | 450 | 14.4 | 71.5 | 29.5 | 10.3 |
| | | | | 490 | 48.0 | 63.5 | 36.5 | 30.4 |
| $K_7PW_8V_2Nb_2O_40$(d)C | 30 | 0.50 | ND | 450 | 16.6 | 75.4 | 24.6 | 12.5 |
| | | | | 490 | 49.2 | 64.2 | 35.8 | 31.6 |

C—calcinated sample
TC—sample used in catalytic test
ND—not determined

Table 4 compares conversion and selectivity results typical of the catalyst family described in this invention note with literature data corresponding to catalytic systems that showed the best performances.

TABLE 4

Comparison with catalytic results of literature

| Catalysts | $M_{cat}$ (g) | Total flow rate (mL/min) | Temperature (° C.) | Propane conversion (%) | Propene selectivity (%) | Reference |
|---|---|---|---|---|---|---|
| 80NiO—$Cs_{2.5}H_{0.5}PMo_{12}O_{40}$ | 0.50 | 50 | 450 | 44 | 45 | A |
| $Cs_{1.5}H_{1.5}PW_{12}O_{40}$ | 1.80 | 31 | 460 | 36 | 30 | A |
| $Cs_{2.5}H_{1.5}PV_1W_{11}O_{40}$ | 0.75 | 15 | 305 | 5 | 26 | B |
| MoVWO | 0.20 | 20 | 400 | 27 | 32 | C |
| 4MoVW/Al | 0.20 | 20 | 400 | 24 | 41 | C |
| $MgMoO_4$ | 2.30 | 133 | 535 | 19 | 62 | D |
| VNM-Fe*[1] | 0.30 | NR | 350 | ~1.5 | 15 | E |
| VNM-Mn*[2] | 1;45 | NR | 350 | ~1.5 | 32 | E |
| $K_7PW_8V_2Nb_2O_{40}$—C(c') | 0.5 | 30 | 490 | 28 | 77 | — |
| $K_4PW_{11}V_1O_{40}$(c)—C | 0.5 | 30 | 490 | 24 | 81 | — |

*[1] 29,127 $h^{-1}$ (GHSV)
*[2] 828 $h^{-1}$ GHSV
NR—not reported

A: Jizhe Zhang, Miao Sun, Chuanjing Cao, Qinghong Zhang, Ye Wang, Huilin Wan, *Appl. Catal. A* 380 (2010) 87.
B: Dimitratos, N.; Vedrine, J.C., *Catal. Today*, 81 (2003) 561.
C: Guerrero-Pérez, M. O.; Herrera, M. C.; Malpartida, I.; Larrubia, M. A.; Alemany, L. J.; Bañares. M. A., *Catal. Today* 126 (2007) 177.
D: Pless, J.D.; Bardin, B.B.; Kim, H.-S.; Ko, D.; Smith, M.S.; Hammond, R.R.; Stair, P.C.; Poeppelmeier, K.R., *J. Catal.*, 223 (2004) 419.
E: Khan, M. I.; Deb, S.; Aydemir, K.; Alwarthan, A. A.; Chattopadhyay, S.; Miller, J. T.; Marshall, C. L., *Catal. Lett.*, 135 (2010) 282.

The process according to present invention is responsible for achieving propene selectivity between 70 and 85%.

The foregoing description of the subject matter of present invention is to be considered only as a possible or possible embodiments, and any particular features therein are to be understood only as something that has been written to facilitate understanding. Accordingly, they are not to be considered as limiting the invention, which is limited to the scope of the following claims.

The invention claimed is:

1. A catalyst for oxidative dehydrogenation of propane, wherein the catalyst is prepared by the following steps:
   a) dissolving alkali or alkaline earth metal oxometalate salts of W, V, and Nb in water at a temperature ranging from 40 to 80° C., wherein the molar ratios W:V and V:Nb are from 2 to 8, to obtain an aqueous solution of polyoxometalates wherein the mass ratio of the polyoxometalates to water is between 30% and 40%;
   b) adding to the aqueous solution of polyoxometalates obtained in step (a) an inorganic acid to a pH between 6.5 and 7.5, and heating the aqueous solution of polyoxometalates to temperatures of 150 to 180° C. for a period of time ranging from 3 to 4 hours;
   c) adding, under constant agitation, to the aqueous solution of polyoxometalates of step (b) a saturated solution of an alkali or alkaline earth metal salt, in an amount of 60% to 80% (v/v) of aqueous solution of polyoxometalates relative to the saturated solution of an alkali or alkaline earth metal salt, to obtain a precipitate of mixed polyoxometalate salts of W, V, and Nb;
   d) filtering and drying the precipitate of mixed polyoxometalate salts obtained in step (c) at a temperature ranging from 25 to 50° C. to obtain a dried mixture of polyoxometalate salts; and
   e) promoting calcination of the dried mixture of polyoxometalate salts obtained in step (d) under air flow at temperatures of from 350 to 550° C. for a period of time from 3 to 5 hours to obtain mixed oxide catalysts of W, V, and Nb having structures of tungsten bronzes.

2. The catalyst of claim 1, wherein the mixed polyoxometalate salts of W, V, and Nb have a Keggin structure of general formula $[PW_{12-x-y}V_xNb_yO_{40}]^{n-}Z^{m+}$, wherein $1 \leq x \leq 6$, $y \leq 3$ and $4 \leq m \leq n \leq 11$, and wherein Z is an alkali metal of: Na, K or Cs or an alkaline earth metal selected from Mg, Ca, and Ba.

3. A process for oxidative dehydrogenation of propane, comprising feeding a fixed bed reactor with the catalyst of claim 1 and a charge comprising a mixture of propane and air in a volume ratio ranging from 1% to 3%, wherein the process is conducted at a gas hourly space velocity (GHSV) of $10^3$ to $10^4$ $h^{-1}$, atmospheric pressure, and a temperature ranging from 300 to 600° C.

* * * * *